United States Patent [19]

Wellman et al.

[11] 4,016,099
[45] Apr. 5, 1977

[54] METHOD OF FORMING ENCAPSULATED TONER PARTICLES

[75] Inventors: Russel E. Wellman, Pittsford; Robert W. Brown, Rochester, both of N.Y.

[73] Assignee: Xerox Corporation, Stamford, Conn.

[22] Filed: Mar. 27, 1972

[21] Appl. No.: 238,528

[52] U.S. Cl. .......................... 252/316; 106/308 M; 252/62.1 P; 252/62.1 L; 252/314; 264/4; 427/221; 427/222
[51] Int. Cl.$^2$ ......................................... B01J 13/02
[58] Field of Search ............. 252/316, 314, 62.1 P, 252/62.1 L; 117/100 A; 424/33; 264/4; 106/308 M; 427/221, 222

[56] References Cited

UNITED STATES PATENTS

| 2,285,093 | 6/1942 | Kokatnur | 252/314 X |
| 3,338,991 | 8/1967 | Insalaco et al. | 117/100 A X |
| 3,415,758 | 12/1968 | Powell et al. | 252/316 |
| 3,523,907 | 8/1970 | Vrancken et al. | 252/316 |

FOREIGN PATENTS OR APPLICATIONS 931,148  7/1963  United Kingdom ............... 252/316

*Primary Examiner*—Richard D. Lovering
*Attorney, Agent, or Firm*—James J. Ralabate; Anthony W. Karambelas

[57] ABSTRACT

A method is provided for forming encapsulated particles comprising forming a dispersion of core material in a solution of wall material in a solvent; drowning said dispersion in at least one liquid which is miscible with the solvent and in which at least the wall material is substantially insoluble, to effect phase-separation of said wall material, whereby said wall material deposits about said core material forming a dilute dispersion of particles comprising said core material encapsulated with said wall material in said liquid, and recovering said encapsulated particles from said liquid.

16 Claims, No Drawings

METHOD OF FORMING ENCAPSULATED TONER PARTICLES

IMPROVED ENCAPSULATION PROCESS

This invention relates to encapsulation processes. More particularly, this invention relates to encapsulation of a core of solid or liquid material within a protective wall by phase-separation of one or both of said core and wall materials from a solvent.

Many different techniques have been developed for encapsulating solid or liquid materials. Generally, these techniques can be regarded as involving the following four basic steps:

1. forming a dispersion of a core material in a medium containing the wall or encapsulating material;
2. depositing the wall material upon the surface of the core material to form capsules;
3. hardening of the capsules to prevent their agglomeration; and
4. recovering the capsules.

The continuous phase or medium in step (1) is normally a solution of the wall material. If the core is liquid, it is dispersed or emulsified in the solution; if, however, the core is solid, it is usually pre-ground to the desired size and then dispersed within the solution. Step (2) generally involves changing the conditions in such a way as to cause phase-separation of the wall material from the continuous wall solution phase. Normally, the wall material is caused to phase-separate as a coherent liquid film around the particles or droplets of the core phase. This liquid or gelatinous wall phase must be hardened (step (3) ), before recovery of the capsules, if the desired product is individual capsules, i.e., a dry powder. Capsule recovery can be effected by filtering, centrifuging and the like, followed by drying. In some instances, the dried product is a caked powder and must be reduced to a free flowing powder by a gentle grinding operation, e.g., sieving.

Two primary and related problems in existing encapsulation processes have been control of particle size and prevention of agglomeration. Particle size is generally established in step (1) or in step (2); it is controlled primarily by varying the type and degree of agitation and also, by use of surfactants and thickeners to modify the interfacial tension and viscosities. Agglomeration of the core material (during step 2) or of the capsules (during steps 2 or 3) can be controlled in the same way as particle size. Experience has shown, however, that conditions which give the desired particle size are not necessarily those suitable for preventing agglomeration later in the process.

Accordingly, it is an object of the present invention to provide an encapsulation process which overcomes the above deficiencies of other prior processes.

It is another object to provide an encapsulation process which has application to a wide variety of liquid phase encapsulations without regard to the manner in which phase separation of the wall material is effected.

It is a further object of the present invention to provide an encapsulation process which prevents the occurrence of agglomeration.

It is a still further object of the present invention to provide an encapsulation process which enables the preparation of toner particles suitable for electrostatographic applications.

These as well as other objects are accomplished by the present invention which provides a method for forming encapsulated particles comprising:

i. forming a dispersion of core material in a solution of wall material in a solvent;

ii. drowning said dispersion in at least one liquid which is miscible with the solvent and in which at least the wall material is substantially insoluble, effecting phase separation of said wall material whereby said wall material deposits about said core material forming a dilute dispersion of particles comprising said core material encapsulated with said wall material in said liquid, and iii. recovering said encapsulated particles from said liquid.

The capsules prepared in accordance with the present invention are especially useful as toner compositions for developer systems employed in electrostatography. For purpose of illustration, this invention will be further described in relation to the preparation of these toner compositions; however, as described hereinbelow, the present invention has broad application.

Electrostatography is perhaps best exemplified by the process of xerography as described in U.S. Pat. No. 2,297,691 to C. F. Carlson. In this process, a photoconductor is first given a uniform electrostatic charge over its surface and is then exposed to an image of activating electromagnetic radiation which selectively dissipates the charge is illuminated areas of the photoconductor while charge in the non-illuminated areas is retained thereby forming a latent electrostatic image. This latent electrostatic image is then developed or made visible by the deposition of finely divided, electroscopic marking material, referred to in the art as "toner" on the surface of the photoconductor, which marking material conforms to the pattern of the latent electrostatic image. The visible image may then be utilized in a number of diverse ways. For example, the image may be viewed in situ on the photoconductive insulator, fixed in place on the photoconductive insulator or transferred to a second surface such as a sheet of paper and fixed in place thereon as desired depending upon whether the photoconductive insulating material is reusable as is the case with amorphous selenium photoconductive insulators or non-reusable as is the case with particulate zinc oxide-binder film type xerographic plates.

Although the Carlson patent describes developing the latent electrostatic image by dusting it with various powders such as lycopodium, gum copal, cumarone-indene resin, various powdered dyes and the like, many other developing materials and techniques have been devised since that time. Some of the development techniques include brush development as described in U.S. Pat. No. 3,015,305 to Hall, powder cloud development as described in U.S. Pat. No. 2,918,900 to Carlson, liquid spray development as described in U.S. Pat. No. 2,551,582 to Carlson, immersion development as described in U.S. Pat. No. 3,010,842 to Ricker, loop development as described in U.S. Pat. No. 2,761,416 to Carlson and donor development as described in U.S. Pat. No. 2,895,847 to Mayo. However, it is more than likely that the commercial xerographic development technique most widely used today is the technique known as cascade development which is described in U.S. Pat. No. 2,618,552 to Wisc. This development technique is carried out by rolling or cascading across the latent electrostatic image bearing surface, a developing mixture composed of relatively large carrier particles, each having a multiplicity of electrostatically adhering fine marking particles, known as toner particles, on its surface. As this mixture cascades or rolls across the image bearing surface the toner particles are electrostatically deposited on the charged portions of the image and not on the uncharged background areas of the image. In addition, toner particles accidently falling on these non-image areas are physically removed therefrom by the electrostatic attraction of carrier particles which pass in close proximity to these unbound toner particles. The result of this development process is an excellent background-free copy of the electrostatic image made up of the toner particles electrostatically clinging to the image surface. As a general rule when any one of these development processes is used with a reusable electrostatographic plate, such as an amorphous selenium plate, the toner particle image is transferred to and fixed on a second layer such as paper sheet in contact with the toner image as described in U.S. Pat. No. 2,576,047 to Schaffert. After the image is transferred from the surface of the amorphous selenium plate, the plate surface may be cleaned and it is then ready for reuse in a subsequent cycle. The toner resins are usually thermoplastics selected to have glass transition temperatures above any ambient temperatures which might be encountered (generally running above 130° F.) and these are fixed to the paper in most cases by radiant heat fusing.

Most other electrostatographic techniques use the abovedescribed or similar development methods employing the same type of marking material or toner, and differ only in the mode of forming the latent electrostatic charge pattern which is developed. (See, for example, U.S. Pat. Nos. 2,576,047 to Schaffert and 3,064,259 to Schwertz.) In another technique, for example, in U.S. Pat. No. 3,081,698 to Childress, a conductive screen with a plurality of apertures which define the image area to be reproduced is spaced opposite a conductive backing electrode and a potential is applied between this backing electrode and the screen such that when finely divided electrostatographic toner particles smaller than the apertures in the screen are applied to the surface of the screen opposite the backing electrode, the electrostatic field set up by the potential source causes the particles to move through the apertures in the screen to form a toner image on the backing electrode in the configuration of the apertures on the screen. Various surfaces may be interposed between the screen and the backing electrode so that the particle image may be intercepted and formed on such interposed surfaces. Regardless of the surface upon which the toner image is deposited, it may be fixed in place upon that surface or transferred to another surface and fixed thereon.

The common feature of all of these electrostatographic systems is that they employ the lines of force from an electric field to control the deposition of finely divided, marking material or toner on a surface, thus forming an image with the toner particles.

In addition to the developing powder or toner materials described in the original Carlson patent, a number of other toner materials have been developed which are especially valuable for use in the newer development techniques including the cascade technique described immediately above. Generally speaking, these new toner materials have comprised various improved resins mixed with different pigments such as carbon black. Some exemplary patents along this line include U.S. Pat. No. 2,659,670 to Copley which describes a toner resin of rosin-modified phenol-formaldehyde, U.S. Pat. No. Re. 25,136 to Carlson which described a toner employing a resin of styrene polymers and copolymers and U.S. Pat. No. 3,079,342 to Insalaco describing a plasticized styrene-methacrylate copolymer resin.

In the past, these toners have generally been prepared by thoroughly mixing the softened resin and pigment to form a uniform dispersion as by blending these ingredients in a rubber mill or the like and the pulverizing this material to form it into small particles. Most frequently, this division of the resin-pigment dispersion has been made by jet pulverization of the material. Although this technique of toner manufacture has produced some very excellent toners, it does tend to have certain shortcomings. For example, it generally produces a rather wide range of particle sizes in the toner particles. Although the average particle size of toner made according to this technique generally ranges between about 10 and about 15 microns, individual particles ranging from sub micron in size to above 30 microns are not infrequently produced. Furthermore, this is a batch process which tends to be slow, expensive, noisy and dusty. In addition, this technique of toner production imposes certain limitations upon the material selected for the toner because the resin-pigment dispersion must be sufficiently friable so that it can be pulverized at an economically feasible rate of production. The problem which arises from this requirement is that when the resin-pigment dispersion is sufficiently friable for really high speed pulverizing, it tends to form an even wider range of particle sizes during pulverization including relatively large percentages of fines. In addition, such highly friable materials are frequently subject to further pulverization or powdering when they are employed for developing in electrostatographic copying apparatus. All other requirements of electrostatographic developers or toners including the requirements that they be stable in storage, non-agglomerative, have the proper triboelectric properties for developing, form good images, do not film or soil the selenium plate and have a low melting point for heat fusing are only compounded by the additional requirements imposed by this toner forming process.

One advantage of the present invention is that it provides a process which can directly produce a colored particle in a range of particle sizes from 1 to 100 microns useful in electrostatographic reproduction systems and which avoids the many cumbersome operational sequences heretofore required.

Any suitable liquid or solid material soluble or dispersible in the same solvent or mixture of solvents as the wall material can be employed as the core material for the encapsulated product of the process of this invention. Typical liquid core materials include water, oils, low molecular weight polymers such as polyesters (e.g., Co-Rezyn 3, available from Interplastic Corporation), polyester based urethane polymers (e.g., Formrez P-910, available from Witco Chemical Corporation), epoxidized bisphenol A acrylate (e.g., Epocryl U-12, available from Shell Chemical Company), the reaction product of dimerized linoleic acid with diamines or polyamines (e.g., Versamid 115 and 140 available from General Mills Chemical Division), polyamides (e.g., Polyamide 315, 235 and 340, available from Union Carbide Corporation), polybutadiene (e.g., Poly B-D, a hydroxy terminated polybutadiene liquid resin available from Sinclair Petrochemicals, Incorporated), silicone gums (e.g., W 981 from Union Carbide), copolyesters of phthalic acid and an alkyl dicarboxylic acid condensed with an alkyl diol (e.g., Santicizers 405 and 411, available from Monsanto Chemical Company), and mixtures thereof. Typical semi-solid core materials include polyesters (e.g., Epon 872, available from Shell Chemical Company), polyester based urethane polymers (e.g., Formrez P-314, P-211 and MG-4 available from Witco Chemical Corporation) epoxidized phenolformaldehyde resin (e.g., Epoxy-Novalak ERLB-0449, available from Union Carbide Corporation), polyisobutylene (e.g., Oppanol B-10, available from Badische Anilin & Soda Fabrik, West Germany) the reaction product of dimerized linoleic acid with diamines or polyamines (e.g., Versamid 100, available from General Mills Chemical Division), and mixtures thereof. Typical solid core materials include polyurethane elastomers (e.g., Estane 5701, 5702, 5710 and 5714 available from B.F. Goodrich Company), polyester based alkyd resins, polyester based urethane polymers (e.g., Formrez P-410, P-610 and L10-72, available from Witco Chemical Corporation), polyamides such as the reaction products of dimerized linoleic acid with diamines or polyamines (e.g., Versamides 712, 948 and 950, available from General Mills Chemical Division), the reaction products of dimer acids with linear diamines (e.g., Emerez 1530, 1538 and 1540, available from Emery Industries, Incorporated), ester gums such as rosin esters and modified rosin esters, polyvinylacetate, the polymeric reaction product of isopropylindenediphenoxypropanol and adipic acid, the polymeric reaction product of isopropylindenediphenoxypropanol and sebacic acid, $C_{36}$ diurea, polyacetaldehyde, styrene butadiene block copolymers (e.g., Kraton 4113, available from Shell Chemical Company), and mixtures thereof. When a single core encapsulated product is sought, core materials having higher surface tension properties than the wall materials should be employed.

Any suitable polymeric material can be employed as the wall material for the encapsulated product of the process of this invention. The wall material can be a homopolymer, a copolymer of two or more monomers or a terpolymer. Typical wall materials include polystyrenes (e.g., PS-2, Styron 666 and 678 available from Dow Chemical Company; Lustrex 99, available from Monsanto Chemical Company), styrene-methacrylate and styrene-acrylate copolymers, polycarbonates (e.g., Lexan 101, a poly-4,4'-dioxydiphenyl-2,2'-propane carbonate) available from General Electric Company), polyethers, low molecular weight polyethylenes, polyesters such as polymeric acrylic acid methacrylic esters, fumarate polyester resins (e.g., Atlac Bisphenol A, available from Atlas Chemical Company), Dion-Iso polyester resins available from Diamond Shamrock Chemical Company, Krumbhaar polyester resins (e.g., K-2200 and K-1979, available from Lawter Chemicals, Incorporated), polyamides such as the reaction product from terephthalic acid and alkyl substituted hexamethylene diamine (e.g., Trogamid T, available from Dynamit Nobel Sales Corporation), the reaction products of dimerized linoleic acid with diamines or polyamines (e.g., Versamid 712, 948 and 950, available from General Mills Chemical Division), the reaction products of dimer acids with linear diamines (e.g., Emerez 1530, 1538, 1540 and 1580 available from Emery Industries, Incorporated), naturally occurring materials such as gelatin, zein, gum arabic and the like, and mixtures thereof.

Basically, any organic polymer including homopolymers and copolymers can be suitably employed as either the core or wall material in the present invention. The selection of a particular polymer for either the wall or core material is dictated by the properties desired in the ultimate encapsulated product. Thus, for example, polymers made from monomers having the characteristic vinyl >C═C< structure can be employed. Illustrative of such polymers are those whose repeating units comprise esters of saturated alcohols with mono and polybasic unsaturated acids such as alkyl acrylates and methacrylates, haloacrylates, diethyl maleate, and mixtures thereof; vinyl and vinylidene halides such as vinyl chloride, vinyl fluoride, vinylidene chloride, vinylidene fluoride, tetrafluoroethylene, chlorotrifluoroethylene and mixtures thereof; vinyl esters such as vinyl acetate, unsaturated aromatics such as styrene and various alkyl styrenes, alpha methylstyrene, parachlorostyrene para bromostyrene, 2,4-dichlorostyrene, vinyl naphthalene, para methoxystyrene and mixtures thereof; unsaturated amides such as acrylamide, methacrylamide and mixtures thereof; unsaturated nitriles such as acrylonitrile, methacrylontrile, haloacrylonitrile, phenylacrylonitrile, vinylidene, cyanide, and mixtures thereof; N-substituted unsaturated amides such as N,N-dimethyl acrylamide, N-methyl acrylamide and mixtures thereof; conjugated butadienes such as butadiene, isoprene and mixtures thereof; unsaturated ethers such as divinyl ether, diallyl ether, vinyl alkyl ether and mixtures thereof; unsaturated ketones such as divinyl ketone, vinyl alkyl ketone and mixtures thereof; unsaturated aldehydes and acetals such as acrolein and its acetals, methacrolein and its acetals, and mixtures thereof; unsaturated heterocyclic compounds such as vinyl pyridine, vinyl furan, vinyl-coumarone, N-vinyl carbazole, and mixtures thereof, unsaturated alicyclic compounds such as vinyl-cyclopentane, vinyl-cyclohexane and mixtures thereof; unsaturated thio compounds such as vinyl thioethers; unsaturated hydrocarbons such as ethylene, propylene, coumarone, indene, terpene, polymerizable hydrocarbon fractions, isobutylene and mixtures thereof; alkyl compounds such as alkyl alcohol, allyl esters, diallyl phthalate, triallylcyanurate and mixtures thereof.

Whether a particular polymer is employed as a core or wall material will depend upon the utimate characteristics desired in the toner particles. For example, in high speed electrostatographic processes, it is often desirable to employ toner particles which are low melting, yet have sufficient surface hardness to enable the toner particles to withstand the rigors of the electrostatographic process. In such instances, for example, a toner comprising a low melting poly(n-butylmethacrylate) core encapsulated with polystyrene would be highly desirable.

In the preparation of electrostatographic toners, wall material resins containing a relatively high percentage of a styrene resin are preferred because better image quality is achieved. The styrene resin may be a homopolymer of styrene or styrene homologues or copolymers of styrene with other monomers containing a single methylene group attached to a carbon atom by a double bond. Thus, typical monomeric materials which may be copolymerized with styrene by addition polymerization include: p-chlorostyrene; vinyl naphthalene; ethylenically unsaturated mono-olefins such as ethylene, propylene, butylene, isobutylene and the like; vinyl esters such as vinyl acetate, vinyl propionate, vinyl benzoate, vinyl butyrate and the like; esters of alpha-methylene aliphatic monocarboxylic acids such as methyl acrylate, ethyl acrylate, n-butylacrylate, isobutyl acrylate, dodecyl acrylate, n-octyl acrylate, 2-chloroethyl acrylate, phenyl acrylate, methyl-alpha-chloracrylate, methyl methacrylate, ethyl methacrylate, butyl methacrylate and the like; acrylonitrile, methacrylontrile, acrylamide, vinyl ethers such as vinyl methyl ether, vinyl isobutyl ether, vinyl ethyl ether, and the like; vinyl ketones such as vinyl methyl ketone, vinyl hexyl ketone, methyl isopropenyl ketone and the like; vinylidene halides such as vinylidene chloride, vinylidene chlorofluoride and the like; and N-vinyl compounds such as N-vinyl pyrrole, N-vinyl carbazole, N-vinyl indole, N-vinyl pyrrolidene and the like; and mixtures thereof. The styrene resins may also be formed by the polymerization of mixtures of two or more of these unsaturated monomeric materials with a styrene monomer.

For an electrostatographic toner, the wall material of the encapsulated toner should have a blocking temperature of at least about 100° F. When the encapsulated toner is characterized by a blocking temperature less than about 100° F., the toner particles tend to agglomerate during storage and machine operation and also from undesirable films on the surface of reusable photoreceptors which adversely affect image quality.

The determination of whether a particular polymer is ultimately the core or wall material is primarily dictated by the solubility characteristics of the solvent employed for either or both of the core and wall materials. The solubility characteristics of the solvent can be altered by changes in temperature or concentration or by addition of one or more liquids which are miscible with the solvent and are non-solvents for either or both the core and wall materials. In the instance wherein the liquid is a non-solvent for both the core and wall materials, it generally is selected to effect phase separation of the core at lower concentrations of non-solvent than are required to effect phase separation of the wall. Similarly, when temperature or concentration changes are relied upon to effect phase separation, the solvent employed must be differentially sensitive either with respect to temperature or concentration to effect phase separation of the core before such separation of the wall.

The present invention relates to a liquid phase encapsulation process in which the wall phase is caused to deposit about the core phase by drowning of the dispersion of the core phase in the wall phase in a liquid which is miscible with the solvent for the wall material and which causes the wall material to phaseseparate. This liquid is also generally a non-solvent for the core material. It has been found in the present invention that the problem of agglomeration during phase-separation and hardening of the wall material can be avoided or substantially reduced by drowning the dispersion of the core phase in the wall phase in a large excess of a non-solvent liquid. Although generally it is only necessary that the core phase undergo phase-separation prior to drowning of the resulting dispersion in the non-solvent liquid, there are instances wherein it is advantageous to partially or completely effect phase-separation of the wall material prior to the drowning step. This will of course depend upon the nature of the particular core and wall materials and solvents and non-solvents employed and particularly upon the non-solvent used for drowning.

Several methods for effecting phase-separation within the dispersions, emulsions or solutions obtained in accordance with the present invention can be suitably employed. For example, in an instance wherein the core and wall materials are dissolved in at least one relatively volatile solvent, phase-separation can be effected by evaporation of the solvent. As the solvent is removed by evaporation, the concentration of the core and wall materials is progressively increased whereby substantially all of the core material preferentially phase-separates as a solvent poor phase. Once phase-separation of the core material is obtained the resulting dispersion of the core material in the wall solution can be drowned or dispersed in a large excess of a liquid which is miscible with the solvent for the wall material and which will effect phase-separation of the wall material whereupon the wall material deposits about the core material and the resulting encapsulated particles undergo hardening as a dilute dispersion in the non-solvent liquid. The encapsulated particles can be easily recovered from the non-solvent liquid as, for example, by filtration. In this instance, as the concentration of the dissolved materials increases, the single phase system becomes increasingly unstable with respect to a two phase system comprised of a solvent poor core phase and a solvent rich wall phase. After phase separation of the core material occurs, the wall phase becomes more concentrated as solvent is continuously removed. It is important for the dispersion of core material in the wall material solution to be drowned in the non-solvent liquid while the viscosity of the dispersion is sufficiently low to permit ready dispersion of said dispersion of core material in the wall material solution in the non-solvent liquid prior to completion of phase separation of the wall material from the solvent.

Alternatively, a solution of core and wall material in a common solvent can be emulsified, and the core phase separated by addition of a non-solvent for the core. Thereafter, the resulting mixture can be drowned in a non-solvent for the wall material to effect phase-separation of the wall material and encapsulation of the core material therewith as described above. In still another embodiment, a solution of core and wall material in a common solvent can be emulsified together with concentrationdependent non-solvent for the core and wall which is less volatile than the solvent and miscible therewith. Upon vaporization of the solvent, the non-solvent becomes more concentrated effecting phaseseparation of the core. Thereafter, the dispersion of the core in the wall material is drowned in a non-solvent liquid as described above to effect encapsulation of the core by the wall material in a dilute environment. In a further embodiment, an insoluble core material can be dispersed in a solution of wall material and the resulting dispersion can be directly drowned in a liquid non-solvent for the wall material effecting phase-separation of the wall material and deposition thereof about the core material.

Basically, this invention comprises the formation of a solution, dispersion or emulsion wherein a dispersion of core material in a solution of wall material is either initially or ultimately obtained. This dispersion can then be directly drowned in a large excess of a liquid which is miscible with the solvent for the wall material and yet, is a non-solvent for the wall material and generally also for the core material, thereby effecting phase-separation of the wall material under conditions wherein the wall material deposits upon and ultimately encapsulates the core material forming a dilute dispersed phase within a continuous phase of the non-solvent liquid. The core and wall materials and solvents therefor are selected so that the change in concentration of solvent or solvents and dissolved materials during solvent removal or upon addition of non-solvents or in some cases, a change in temperature within the dispersed solution, will cause the core material to phase-separate as a solvent poor, high surface tension phase in a solution of wall material. Upon drowning the resulting dispersion in a non-solvent liquid, the wall material will phase-separate and encapsulate the core material and ultimately form a hardened capsule shell or wall about the core. The separated core material phase and the separated wall material phase can be solvent poor phases and not solvent free phases.

It is considered important in the present invention that the core dispersion in the wall material solution be drowned and dispersed in sufficient nonsolvent liquid to preclude agglomeration of the encapsulated particles during the period of phase-separation of the wall material from the solvent since during this period the wall material is tacky and can give rise to the problems of agglomeration which are sought to be avoided herein. Since the encapsulated particles form a dilute dispersed phase within a continuous nonsolvent phase, the wall material is allowed to harden in a dilute environment which essentially precludes the occurrence of agglomeration. Generally, volume ratios of the non-solvent liquid to the core dispersion to be drowned therein ranging above at least about 4:1 have been found suitable. Of course, the volume ratio can vary depending upon the particular materials and conditions employed; however, volume ratios ranging from about 4:1 to about 8:1 or above are preferred. The encapsulated particles produced can be recovered from the continuous non-solvent phase in a dry, free flowing form by any conventional or suitable means such as filtering, evaporating the non-solvents and the like.

The desired core and wall materials can be selected first on the basis of desired capsule properties. The solvent or mixture of solvents can then be selected to give the desired encapsulation. This selection is made on the basis fo core and wall material solubility and solvent volatility. Heretofore, after the desired core and wall materials have been selected, experiments were necessary to determine the solubility characteristics of the materials. Once these general characteristics were established it was necessary to investigate potential solvent combinations in greater detail by determining solvent ratios at the cloud point. In simpler cases, theser preliminary experiments were sufficient to permit selection of a suitable solvent system; however, in more complex cases where either the mutual solubility of core and wall materials is limited or difficulty is encountered in finding conditions for phase-separation of the core without also precipitating the wall material use must be made of solubility area plots as described in "A Three Dimensional Approach To Solubility," James D. Crowley et al, Journal of Paint Technology, Volume 38, No. 496, pages 269–280 (May, 1966). One of the principal advantages of the drowning technique of the present invention is that encapsulation procedures can be quickly and easily determined for never-before tried core/wall combinations. Thus, the present invention provides a useful research tool for the obtainment and development of encapsulated toner materials.

The particular solvent employed will, of course, vary depending upon the polymers employed. However, the suitability of a particular solvent for particular core and wall polymers can be readily determined with the main consideration being the solubility of the core and wall materials in such solvent or mixture of the solvents and the evaporation characteristics of the solvent or mixture of solvents such as to permit sequential phase-separation upon solvent removal. Typical solvents which can be employed are, for example, water, aromatic hydrocarbons such as benzene, chlorobenzene, toluene and the like, cyclic and acyclic aliphatic hydrocarbons such as cyclohexane, pentane, hexane, heptane and the like halogenated aliphatics such as methylene chloride, ethylene dichloride, dichloromethane, chloroform, carbon tetrachloride, alcohols such as methanol, ethanol, propanol, isopropanol, butanol and the like, methyl ethyl ketone, ethyl acetate, tetrahydrofuran, acetone, dimethylformamide and the like.

The particular order of addition of the components prior to drowning is not considered important; however, as a matter of convenience the desired wall material is generally first dissolved in the solvent and the desired core material is then either dissolved or dispersed therein. In instances wherein the core material is soluble in the selected solvent, the particular order of addition of core and wall materials is of no consequence.

The ratio of core and wall materials to the solvent system generally can be any practical dilution. Thus, the dissolved solids content of the solution may range from about 0.5 percent to about 50.0 percent by weight based on the solution but this can also vary a general limitation being phase-separation of the core material and another being practicality of the solute concentration.

The ratio of wall material to core material can be any suitable value and generally is varied with the thickness, strength, porosity, and solubility characteristics of wall desired. Thus, generally, the ratio of wall material to core material may be between about 99 parts by weight of wall material to about 1 part by weight of core material and about 1 part by weight of wall material to about 99 parts by weight of core material. However, the preferred range is between a ratio of about 7 parts by weight of wall material to about 1 part by weight of core material and about 1 part by weight of wall material to about 7 parts by weight of core material as encapsulated particles having the best surface characteristics are obtained. In general, the thickness of the wall material can be controlled by the ratio of the amount of core material to be encapsulated to the amount of wall material. Thus, if a thicker wall layer is desired, more wall material should be used since the ratio of wall to core material remains constant during the process of this invention. In addition, the size of the encapsulated particle also affects the wall thickness since the smaller the particle, the smaller the wall thickness at a constant core to wall ratio.

The solubilities of the core and wall materials that can be employed in the method of this invention can vary considerably in a selected solvent system. For example, completely hydrolyzed styrene-maleic anhydride polymer is about 2.0 percent by weight soluble in water but at least about 20.0 percent by weight soluble in a 50:50 volume mixture of methanol and water.

Thus, solutions of the desired core and wall materials can be prepared in relatively dilute or in concentrated form in water alone or by choice of solvent, or mixtures thereof, depending upon the relative solubilities of the materials employed. Further, the concentration of core and wall materials can be increased by the addition of a solubilizing agent, e.g., another hydrophilic liquid such as methanol or ethanol.

Once the solution or dispersion of core and wall materials is prepared or simultaneously with the preparation thereof, a colorant can be admixed therewith if a colored toner particle is desired.

The core, wall, or both the core and wall materials can be pigmented or dyed, or pigmented and dyed by addition of suitable pigment or dye or both pigment and dye to the solution of core and wall materials. The pigment or dye, or pigment and dye, in many cases can be concentrated in the core or in the wall material or at the interface between the core and wall materials by proper selection of colorant and solution system having the desired surface interaction, and solubility properties. Thus, a dye must be insoluble in the non-solvent liquid and will generally be concentrated in the phase, core or wall, in which it is soluble. The solubilities obtaining during the encapsulation could conceivably force the dye elsewhere but this would be a special case. For example, a dye soluble in the core material, insoluble in the wall material but soluble in the solvent-rich wall phase and insoluble in the non-solvent, would probably be concentrated on the exterior of the capsules. In some cases, dyes will form separate phases like pigment particles because of insufficient solubility in the core and wall materials, that is, where the dye is soluble in the solution but has little or no solubility in either core or wall material after removal of the solvent. In these cases, the solubility of the dye in the core and wall materials rich, but still fluid, phases will control where the dye particles are concentrated in the dry capsule.

A pigment will generally be concentrated in the core or wall material which preferentially adsorbs on the pigment from solution. With most carbon blacks, and probably most pigments, the tendency to adsorb will increase with increased polarity and hydrogen bonding of the polymer. Also the material which is separating as a solvent poor phase is more likely to be absorbed. Thus, for example, in a system employing the polymeric reaction product of isopropylidenediphenoxypropanol and adipic acid as the core material and polystyrene as the wall material with carbon black as the colorant, all three factors favor absorption of the polymeric reaction product of isopropylidenediphenoxypropanol and adipic acid, therefore the carbon black concentrates in the core phase. With polyisobutylene as the core material and poly-(4,4'-dioxydiphenyl-2,2'-propane carbonate) as the wall material, the polyisobutylene has little tendency to be adsorbed even as a solvent poor phase and the carbon black remains suspended in the solution of wall material to be deposited in the capsule wall. Surfactants and stabilizers, including materials added for other reasons such as core plasticizers, can change the adsorption characteristics and therefore result in the pigment being concentrated in a different phase.

Any suitable colorant, whether insoluble pigment or soluble dye, can be dispersed or dissolved in the solvent. If desired, especially for photoelectrophoretic processes, electrically photosensitive colorants can also be employed. Additionally, combinations of pigments and/or dyes can be employed to obtain specific coloration effects.

Suitable pigments for use in the present invention include, for example, carbon blacks, Algol Yellow, Pigment Yellow 6, Benzidine Yellow, Vulcan Fast Yellow GR, Indofast Orange, Ortho Nitroaniline Orange, Vulcan Fast Orange GG, Irgazine Red, Paranitraniline Red, Toluidine Red, Permanent Carmine FB, Permanent Bordeaux FRR, Romanesta Red, Pigment Orange R, Vulcan Fast Rubine BF, Lake Red D, Lithol Red 2G, Double Ponceau R, Calamine Red MB, Pigment Scarlet 3B, Acid Alizarine Red B, Rhodamine 6G, Rhodamine B Lake, Methyl Violet B Lake, Gentian Violet Lake, Quinizarin, Victoria Pure Blue BO Lake, Ethylviolet Lake, Phthalocyanine Blue B Pr, Pigment Blue BCS, Peacock Blue Lake, Brilliant Green B, and the like.

Typical photosensitive organic materials include substituted and unsubstituted organic pigments such as phthalocyanines, for example, copper phthalocyanine, beta form of metal-free phthalocyanine; tetrachlorophthalocyanine; and x-form of metal-free phthalocyanine; quinacridones, as, for example, 2,9-dimethyl quinacridone; 4,11-dimethyl quinacridone; 3,10-dichloro-6,13-dihydroquinacridone; 2,9-dimethoxy-6,13-dihydroquinacridone and 2,4,9,11-tetrachloroquinacridone; anthraquinones such as 1,5-bis-(beta-phenylethylamino)anthraquinone; 1,5-bis-(3'-methoxypropylamino)anthraquinone; 1,2,5,6-di-(C,C'-diphenyl)-thiazole-anthraquinone; 4-(2'-hydroxyphenylmethoxyamino)anthraquinonyl-amino-6-(1''-pyrenyl)-triazine; 2,4,6-tri-(1',1'',1'''-pyrenyl)-triazine; azo compounds such as 2,4,6-tris(N-ethyl-p-amino-phenylazo)phloroglucinol; 1,3,5,7-tetrahydroxy-2,4,6,8-tetra(N-methyl-N-hydroxyethyl-p-amino-phenylazo)naphthalene; 1,3,5-trihydroxy-2,4,6-tri(3'-nitro-N-methyl-N-hydroxy-methyl-4'-amino-phenylazo)benzene; metal salts and lakes of azo dyes such as calcium lake of 6-bromo-1-(1'-sulfo-2-naphthyl-azo)-2-naphthol; calcium lake of 1-(2'-azonaphthalene-1'-sulfonic acid)-2-naphthol; calcium lake of 1-(4'-ethyl-5'-chloroazobenzene-2'-sulfonic acid)-2-hydroxy-3-naphthoic acid; and mixtures thereof. Other organic pigments include polyvinylcarbazole; trisodium salt of 2-carboxyl phenylazo(2-naphthiol-3,6-disulfonic acid; N-isopropyl- carbazole; 3-benzylidene-aminocarbazole; 3-aminocarbazole; 1-(4'-methyl-5'-chloro-2'-sulfonic acid)azobenzene-2-hydroxy-3-naphthoic acid; N-2''-pyridyl-8,13-dioxodinaphtho-(2,1-b,2',3'-d)-furan-6-carboxamide; 2-amino-5-chloro-p-toluene sulfonic acid and the like.

The x-form of metal free phthalocyanine as described in U.S. Pat. No. Re. 27.117 is preferred because of its excellent photosensitivity and intense coloration.

Typical inorganic photosensitive compositions include cadmium sulfide, cadmium selenide, cadmium sulfo-selenide, zinc oxide, zinc sulfide, sulfur, selenium, antimony sulfide, lead oxide, lead sulfide, arsenic sulfide, arsenic-selenium, and mixtures thereof.

Any suitable dye or class of dyes may be used. Typical acid dyes include, for example, anthraquinones such as C.I. Acid Blue 127, triphenylmethanes such as C.I. Acid Blue 103, azine dyes such as C.I. Acid Blue 98, xanthenes such as C.I. Acid Violet 9, C.I. Acid Red 92 and the like, nitroso dyes such as C.I. Acid Green 1, monoazo dyes such as C.I. Acid Yellow 29, diazo dyes such as C.I. Acid Green 20, quinolines such as C.I.

Acid Yellow 3, diazo dyes such as C.I. Acid Orange 79, and the like.

Typical basic dyes include thiazoles such as C.I. Basic Yellow 1, ketone amine dyes such as C.I. Basic Yellow 2, acridines such as C.I. Basic Yellow 4 and the like.

Typical dispersed dyes include nitro-acetamine dyes such as Yellow 2 RZ — C.I. Disperse Yellow 1, azo dyes such as C.I. Disperse Orange 3, Disperse Red 1, C.I. Disperse Black 9, C.I. Blacks 18, 19, 16, 1, 7, 12, 24 and 27, anthraquinones such as C.I. Disperse Violet Celanthrene Red, C.I. Disperse Blue 9, diazo dyes such as C.I. Food Black 1 and amino ketone dyes such as C.I. Disperse Green 1.

The wall and core materials as well as the colorant can be dispersed and/or dissolved in the solvent by admixing said materials with the solvent under intensive agitation as obtained, for example, in a high speed, high shear mixer such as a Waring blender equipped with a Polytron high shear head, a homogenizing mixer or the like, capable of a speed of from about 1000 to 15,000 rpm.

The amount of colorant added for toner preparation can range from about 3 to about 20 weight percent based on the total weight of the colored encapsulated particle. If the colorant is a dye, substantially smaller quantities of colorant can be used. Preferably, prior to dispersion of the colorant in the solvent, dispersing aids can be added to the solvent such as surfactants, dispersants and the like to assist in effecting a uniform dispersion. It has been found that increasing the viscosity of the solution prior to addition of the colorant is an effective means of stabilizing the colorant dispersion. Typical oil soluble surfactants which can be employed to aid the dispersion of colorant are, for example, bis(trialkyl)esters of sodium sulfosuccinic acid, nonyl phenyl polyethoxy ethanol, alkylated polyvinyl pyrrolidone, phosphate monoglyceride, alkanolamides, sorbitan esters and the like. Generally, sufficient dispersing aid is from about 0.1 to about 50 weight percent of the colorant.

Once the colorant/wall-core dispersion is obtained, phase-separation of the core material is effected as described hereinabove. If the core material already exists as a dispersed phase, this step will of course be unnecessary. Once the dispersion is thus obtained it can be drowned in a liquid which is miscible with the solvent for the wall material and which effects phase-separation of the wall material. Typical liquids which can be so employed include, for example, water, alcohols such as methanol, ethanol, isopropanol and butanol, ketones such as acetone, aliphatic hydrocarbons such as cyclohexane and heptane, amides such as dimethylformamide as well as mixtures of these liquids. Generally, the dispersion of core material and wall material is drowned in the non-solvent liquid while the non-solvent liquid is undergoing intensive agitation as obtained, for example, in a high speed, high shear mixer such as a Waring blender, a homogenizing mixer or the like. It is important in obtaining good particle size as well as in preventing agglomeration to obtain uniform dispersion of the dispersion of core material and wall solution before the completion of phase-separation of wall material and deposition thereof about the core material. In this manner, the wall material phase-separates, deposits about the core material and its surface is hardened by the non-solvent liquid before significant agglomeration can occur. Sufficient non-solvent liquid is used to ensure that at the end of the encapsulation the continuous phase is dilute in solvent and the solid material is a dilute dispersion in the liquid.

Employing the process of the present invention, encapsulated toner particles containing a colorant which can be photosensitive can be readily obtained. Advantageously, the particles can be surface hardened by proper selection of the wall material enabling the use of low melting resins which are desirable for rapid fusing operations.

The encapsulated toner compositions obtained in accordance with the present invention can be admixed with solid or non-solvent liquid vehicles therefor to form electrostatographic developer compositions. In general, successful results have been obtained with from about 10 to about 200 parts by weight of either solid or liquid vehicle to about 1 part by weight of toner. Preferably, the vehicle to toner ratio ranges from about 50 to 1 to about 150 to 1. In such preferred compositions the vehicle acts effectively to remove any toner particles which might tend to adhere to a non-image area and the toner itself forms dense readily transferable and fusible images.

Solid vehicles are generally in the form of granular carrier particles which are larger than the toner particles and are shaped to roll across the image-bearing surface. Generally speaking, the particles should be of sufficient size so that their gravitation or momentum force is greater than the force of attraction of the toner in the charged areas where the toner is retained on the plate in order that the granular carrier particles will not be retained by the toner particles, while, at the same time, the toner particles are attrached and held, or repelled, as the case may be, by the charged or uncharged areas of the plate since said toner particles acquire a charge of opposite polarity to the charge of both the granular carrier particles and the plate. It has been found best to use granular carrier particles of a size larger than about 10 microns, usually between 30 and about 1,000 microns, and toner particles of a size from about 1 to 20 microns. The granular carrier particles may, if desired, be somewhat larger or smaller as long as the proper size relationship to the electroscopic toner is maintained so that the granular carrier particles will flow easily over the image surface by gravity when the plate is inclined without requiring additional means or measures to remove them.

Typical carrier materials include: sodium chloride, ammonium chloride, potassium chlorate, granular zircon, granular silicon, methylmethacrylate, glass, silicon dioxide, flintshot, iron, steel, ferrite, nickel, carborundum, and mixtures thereof. Many of the foregoing and other typical carriers are described by L. E. Walkup et al. in U.S. Pat. No. 2,638,416 and E. M. Wise in U.S. Pat. No. 2,618,552.

When it is desired to employ a liquid developer composition, the toner compositions of the present invention can be incorporated in any conventional liquid vehicle which is a non-solvent for and non-reactive with the polymer and which has a volume resistivity above about $10^{10}$ ohm-cm and a dielectric constant greater than 2.5. In addition, the liquid vehicle should, if possible, be one which does not have an appreciable toxicity and which is not too flammable. It is also considered desirable to employ a liquid which is neither malodorous nor highly colored. It is essential that the liquid vehicle be inert to the material which bears the latent electrostatic image to be developed. Suitable liquid carriers are, for example, kerosene, turpentine, benzene, cyclohexane, carbon tetrachloride, silicones, fluorinated hydrocarbons such as tetrachlorodifluoroethane, trichlorotrifluoroethane and the like. Other suitable liquid vehicles are described in U.S. Pat. No. 2,899,335.

In another aspect of the present invention, an electrostatographic process is provided which employs the developer compositions of this invention. The toner develops the latent electrostatic image on the image bearing surface and can be fused thereon or can be subsequently electrostatically transferred to a substrate and then fused on the substrate to form a permanent image thereon.

The process of the present invention is particularly advantageous for preparing solid coated toner material which is in an extremely fine state of subdivision, for example, from about 0.5 to about 35 microns in diameter. The particular particle size is not critical to the process of the invention, but is determined by the use to which the coated particle is to be employed. For example, capsules containing powders or liquids on the order of about 0.5 to about 10 micron in size are desirable for vitamins and other food supplements, for substances to be incorporated into cosmetic formulations and for insecticides. A powdered material up to about 200 micron size is a desirable size for rodenticides.

The encapsulated products of the present invention also find applications due to their unique properties in the formulation of compositions for widely diversified fields of use. In the cosmetic field, products such as soap bars, lotions and creams can be formulated containing encapsulated water soluble ingredients which would be unstable or incompatible in unencapsulated form in the presence of other ingredients of the particular formulation. For example, since certain antibacterials such as the chlorinated phenols and neomycin sulfate are incompatible on prolonged contact with soap, the present invention makes possible the formulation of a soap bar containing both of these ingredients.

In the agricultural field, encapsulated food supplements and medicaments can be advantageously formulated. For example, water soluble fertilizers such as ammonium nitrate, urea and superphosphate can be encapsulated for application to the soil when a slow release or extended action is desirable, e.g., where rapid release would "burn" the vegetation. For the control of pests, encapsulated insecticides can be deposited on vegetation or in the soil without harm to the vegetation; moreover, the insecticide is not dissolved and washed away by moisture or rain, thereby allowing the insecticide to remain where deposited until ingested by the insect. Antihelminthic agents such as piperazine phosphate or citrate, and methyl rosaniline chloride when encapsulated can be incorporated into feed material for domestic animals, the encapsulated antihelminthic thereby being tasteless in the feed and also protected from decomposition during storage of the feed. Rodenticides such as calcium cyanide, thallium sulfate and sodium fluoroacetate, which are unstable in the presence of moisture or have an odor or taste repellent to the rodent are advantageously encapsulated.

Vitamins, minerals, amino acids and other food supplements, when encapsulated can be incorporated in animal feeds and be protected from decomposition during storage periods from such adverse conditions as air, moisture, and incompatible ingredients in the feed composition itself. In a similar manner, food supplements can be incorporated in compositions for human use.

The present invention finds application in medical treatment of both animals and humans. Medicaments can be encapsulated by the method of the present invention to give a sustained release upon ingestion with resultant sustained therapeutic action. Coatings which will not dissolve in the stomach can be formulated to overcome the problem of gastric irritation or nausea caused by such medicaments as emetine hydrochloride, quinacrine hydrochloride and paraamino-salicyclic acid. Similarly, medicaments such as penicillin and certain glandular extracts which are inactivated by the acid condition or enzymes encountered in the stomach are advantageously encapsulated.

The following examples further define, describe and compare methods of preparing the encapsulated materials of the present invention and of utilizing them as toner compositions and in developer compositions to develop electrostatic latent images. Parts and percentages are by weight unless otherwise indicated.

As used in the following examples, the term "stick point" means the temperature at which a material adheres to a metallic substrate; for example, a continuous line of sample is equilibrated on a Kofler Hot Bench for about two hours and then greatly brushed away. This "stick point" is the lowest temperature at which the sample "sticks" to the metallic plate of the hot bench.

EXAMPLE 1

To a Waring blender are charged 40 milliliters of acetone, 15 grams of a 50/50 copolymer of docosyl acrylate and styrene and 15 grams of a 75/25 copolymer of styrene and n-butyl methacrylate. The ingredients in the blender are heated to 45° – 50° C with no agitation. After the ingredients reach the desired temperature, they are then stirred within the Waring blender at high speed. Thereafter, 3.0 grams of Monarch 74 carbon black are added to the mixture with stirring. The temperature is then lowered by the addition of 210 milliliters of acetone. The resulting mixture is then divided into portions and each portion is drowned in a large excess of ice water contained in a Waring blender. Thereafter, the contents of the blender are separated by filtration. The resulting encapsulated particles are evaluated on a Kofler Hot Bench and are found to have a stick point of about 65° C.

Thus, the encapsulated particles behave essentially as the styrene/n-butyl methacrylate copolymer indicating that the core of the docosyl acrylate/styrene copolymer is completely encapsulated. There is no observable agglomeration. 27.1 grams of encapsulated material are recovered as the filter cake.

EXAMPLE 2

50 milliliters of a 10% solution of polystyrene in toluene and 50 milliliters of a 10% solution of poly(-hexamethylene sebacate) in toluene are mixed together in a beaker equipped with a magnetic stirrer. Thereafter, 1.0 gram of Monarch 74 carbon black is dispersed in this solution employing magnetic stirring. The solution is cooled to −10° C with continuous magnetic stirring at which point the poly(hexamethylene sebacate) has phase-separated. The resulting dispersion is then drowned in a large excess of n-butanol in a Waring blender with continuous high speed agitation. About 200 milliliters of methanol are added during the drowning operation. Thereafter, the contents of the Waring blender are separated by filtration and the filler cake comprising encapsulated particles is dispersed in methanol with magnetic stirring and allowed to wash for about 1 hour. Thereafter the encapsulated particles are recovered by filtration and air dried.

The encapsulated particles appear well encapsulated and exhibit a stick point on the Kofler Hot Bench of about 95° C. The encapsulated particles appeared to be pressure fixable.

EXAMPLE 3

This example illustrates the encapsulation of a liquid ink comprising a liquid hydroxy-terminated butadiene-styrene copolymer, and carbon black.

Six grams of Sinclair CS-15, a liquid polymer comprising a hydroxy-terminated butadiene-styrene copolymer is dissolved in 100 milliliters of a 10 weight percent solution of polystyrene in chloroform. All of the polymer goes into solution. 95 milliliters of the resulting solution are added to 400 milliliters of acetone in a beaker equipped with a magnetic stirrer under continuous agitation. The mixture becomes very cloudy; however, no observable agglomeration occurs. 1.33 grams of Monarch 74 carbon black are added and stirred into the mixture.

Thereafter, three equal portions of the resulting dispersion are each drowned in about 600 milliliters of methanol in a Waring blender operating at high speed. The resulting encapsulated particles appear light gray and fine and are recovered by filtration. The resulting filter cake is reslurried in methanol in a Waring blender and the encapsulated particles are then recovered by filtration and left to dry in an evaporating dish.

One part of the resulting encapsulated particles is admixed with 99 parts of 450 micron steel carriers coated with a terpolymer of styrene, methyl methacrylate and vinyl triethoxysilane, to form an electrostatographic developer mixture. The developer mixture is print tested in a Model D electrostatographic reproduction apparatus (available from Xerox Corporation, Rochester, N.Y.). Good copies are obtained.

EXAMPLE 1

This example illustrates the encapsulation of a liquid.

5 milliliters of paraffin oil and 1.0 gram of Monarch 74 carbon black are dispersed in 100 milliliters of a 5% solution of a 75/25 copolymer of styrene and n-butyl methacrylate in acetone in a Waring blender at low speed. The resulting dispersion is then drowned in 500 milliliters of water in a Waring blender operating at high speed. The resulting encapsulated particles are separated from the slurry by filtration and are air dried.

The encapsulated particles appear as a fine gray powder and provide an excellent encapsulation of a liquid. The carbon black appears to be sandwiched between the core and the wall.

EXAMPLE 5

17.5 milliliters of a 10% solution of a hydroxy-terminated polybutadiene in toluene and 35 milliliters of a 20% solution of polystyrene in toluene are admixed in a Waring blender. 160 milliliters of acetone are then added to the blender to effect phase-separation of the hydroxy-terminated polybutadiene. 0.9 grams of Monarch 74 carbon black is dispersed in the dispersion with the blender operating at low speed. The resulting mixture is then drowned in 500 milliliters of a 90/10 methanol/water solution in a Waring blender operating at low speed. The resulting encapsulated particles are separated from the slurry by filtration and are washed in 500 milliliters of a 90/10 methanol/water solution in a Waring blender at low speed. The encapsulated particles are then recovered by filtration and dried.

The encapsulated particles are gray and powdery after drying and appear well encapsulated.

EXAMPLE 6

25 milliliters of a 10% solution of a hydroxy-terminated polybutadiene in chloroform and 50 milliliters of a 10% solution of polystyrene in chloroform are admixed in a beaker by magnetic stirring. The resulting solution together with 400 milliliters of acetone and 0.75 gram of Monarch 74 carbon black are admixed in a Waring blender at low speed. The resulting mixture is divided into two equal portions and each portion is drowned in 500 milliliters of methanol in a Waring blender operating at low speed. Thereafter the portions are recombined during filtration and the resulting filter cake is washed in 500 milliliters of methanol in a Waring blender at low speed. The resulting encapsulated particles are recovered by filtration and dried. These particles are gray in color and powdery. The encapsulated particles can be easily pressure-fixed with a spatula.

EXAMPLE 7

This example illustrates the use of mutual incompatibility of polymers in a solvent to effect phase-separation.

1.75 grams of a hydroxy-terminated polybutadiene are dissolved in 50 milliliters of a 10% solution of polystyrene in methyl ethyl ketone in a beaker equipped with a magnetic stirrer. The solution is heated to 75° C at which temperature it appears as a clear, colorless solution. The solution is then heated with magnetic stirring and boiled down to a total volume of about 20 milliliters. At this point, the solution appears cloudy and viscous. The resulting hot dispersion is then drowned in about 300 milliliters of methanol in a Waring blender operating at low speed. The resulting dispersion is separated by filtration and the recovered encapsulated particles are dried. The stick point of the encapsulated particles on a Kofler Hot Bench is about 95° C indicating encapsulation of the core with a wall of polystyrene.

EXAMPLE 8

25 milliliters of a 10% solution of poly(isodecyl methacrylate) in o-dichlorobenzene and 25 milliliters of a 10% solution of polystyrene in o-dichlorobenzene are mixed together in a beaker equipped with a magnetic stirrer. 0.5 grams of Monarch 74 carbon black are dispersed in the resulting solution with magnetic stirring. 50 milliliters of acetonitrile is then added to the solution and appears to result in some slight agglomeration; however, there is little settling and the material remains well dispersed. The dispersion is then drowned in 500 milliliters of methanol in a Waring blender operating at low speed. The resulting encapsulated particles are filtered and then washed in about 300 milliliters of methanol in a Waring blender and then finally filtered and dried.

The encapsulated particles appear light gray with black spots. The encapsulated particles are easily pressure-fixed using a spatula and can be removed from paper only with difficulty.

EXAMPLE 9

50 milliliters of a 20% solution of poly(hexamethylene sebacate) in toluene and 50 milliliters of a 20% solution of polystyrene in toluene are mixed together in a beaker equipped with a magnetic stirrer. 1.0 gram of Monarch 74 carbon black is dispersed in this solution with stirring. The solution is cooled to −10° C with continuous magnetic stirring. The cold dispersion is drowned in 300 milliliters of isopropanol in a Waring blender at low speed and 100 milliliters of methanol are added during the drowning operation. The encapsulated particles are separated from the slurry by filtration and are washed in 500 milliliters of methanol in a Waring blender at low speed. The encapsulated particles are again filtered and the filter cake is vacuum dried at 40° C.

The encapsulated particles are light gray in color and exhibit a stick point on the Kofler Hot Bench of 96° C indicating good encapsulation with polystyrene. A developer composition is prepared employing one part of the encapsulated particles and 99 parts of 250 micron glass carrier together with 1% Aerosil R-972, (a methylated, colloidal, pyrogenic, fumed silica available from Degussa, Inc.). The resulting developer is print tested in a Model D electrostatographic reproduction apparatus. The developer is found to result in the obtainment of good copies.

EXAMPLE 10

16 milliliters of a 1/1 mixture of polyethylene azeleate and polystyrene in a 1/1 mixture of acetone and cyclohexane in a beaker equipped with a magnetic stirrer. 1.0 gram of Mogul-L carbon black is dispersed in the resulting clear yellow solution with magnetic stirring. The resulting dispersion is boilded down to a total volume of 110 milliliters and is then drowned in 300 milliliters of isopropanol in a Waring blender operating at low speed. During the drowning operation, 100 milliliters of methanol are added to the blender. Thereafter, the resulting encapsulated particles are recovered by filtration. The filter cake is washed in 400 milliliters of methanol in a Waring blender operating at low speed. The encapsulated particles are recovered by filtration and vacuum dried at room temperature.

The encapsulated particles appear as a light gray powder. The stick point on a Kofler Hot Bench is 95° C indicating complete encapsulation by polystyrene. An electrostatographic developer is prepared by admixing one part of the resulting encapsulated particles with 99 parts of 250 micron homogeneous glass carrier. The developer is print tested in a Model D electrostatographic reproduction apparatus and is found to provide useful prints.

EXAMPLE 11

This example illustrates the encapsulation of a solid within a wall of polystyrene.

10.0 grams of anthracite having a particle size less than about 44 microns is dispersed in 50 milliliters of a 20% solution of polystyrene in chloroform in a beaker equipped with a magnetic stirrer. The resulting dispersion is drowned in 300 milliliters of isopropanol in a Waring blender operating at low speed. During the drowning operation 100 milliliters of methanol are added. The encapsulated particles are recovered by filtration and washed in 400 milliliters of methanol in a Waring blender operating at low speed. The resulting encapsulated particles are recovered by filtration and vacuum dried at 40° C. The encapsulated particles appear medium gray in color.

Although specific materials and conditions are set forth in the above exemplary processes in making and using the encapsulated particles of this invention, these are merely intended as illustrations of the present invention. Various other polymers, solvents and conditions such as those listed above may be substituted in the examples with similar results.

Other modifications of the present invention will occur to those skilled in the art upon a reading of the present disclosure. These are intended to be included within the scope of this invention.

What is claimed is:
1. A method of forming encapsulated toner particles comprising:
   a. Forming a dispersion of core material in a solution of wall material in a solvent by dissolving said core material and said wall material in a solvent to form a solution and effecting preferential phase-separation of said core material from said solution, said dispersion also containing a colorant selected from the group consisting of dyes and pigments and mixtures thereof dispersed therein;
   b. Drowning said dispersion in at least one liquid which is miscible with the solvent and in which at least the wall material is substantially insoluble to effect phase-separation of said wall material forming a dilute dispersion of particles comprising said core material encapsulated with said wall material in said liquid and;
   c. Recovering said colored encapsulated toner particles from said liquid.
2. The method as defined in claim 1 wherein the core material is an organic polymer.
3. The method as defined in claim 1 wherein the wall material is an organic polymer.
4. The method as defined in claim 1 wherein the wall material comprises a styrene polymer.
5. The method as defined in claim 1 wherein the wall material exhibits a blocking temperature of at least about 100° F.
6. The method as defined in claim 1 wherein the liquid which is miscible with the solvent is a non-solvent for the core material.
7. The method as defined in claim 1 wherein phase-separation of the core material is effected by evaporation of the solvent.
8. The method as defined in claim 1 wherein upon drowning, said dispersion is substantially uniformly dispersed in the non-solvent liquid prior to substantial completion of phase-separation of the wall material from the solvent therefor.
9. The method as defined in claim 1 wherein the volume ratio of the liquid in which the wall material is substantially insoluble to the core dispersion to be drowned therein, ranges above at least about 4:1.
10. The method as defined in claim 9 wherein the volume ratio ranges from about 4:1 to about 8:1.
11. The method as defined in claim 1 wherein the dissolved solids content of the solution of core and wall material in a solvent ranges from about 0.5 to about 50% by weight based on the total weight of solution.

12. The method as defined in claim 1 wherein the weight ratio of wall material to core material ranges from about 99:1 to about 1:99.

13. The method as defined in claim 1 wherein the pigment is carbon black.

14. The method as defined in claim 1 wherein the colorant is added in amounts ranging from about 3 to about 20 weight percent based on the total weight of the colored encapsulated toner particle.

15. The method as defined in claim 1 wherein the liquid which is miscible with the solvent for the wall material and which affects phase-separation of the wall material is selected from the group consisting of water, alcohols, and mixtures thereof.

16. A method of forming encapsulated toner particles comprising:

a. Forming a dispersion of core material in a solution of wall material in a solvent by emulsifying a solution of core and wall material in a common solvent and effecting phase-separation of core material by addition of a non-solvent for said core material, said dispersion also containing a colorant selected from the group consisting of dyes and pigments and mixtures thereof dispersed therein;

b. Drowning said dispersion in at least one liquid which is miscible with the solvent and in which at least the wall material is substantially insoluble to effect phase-separation of said wall material forming a dilute dispersion of particles comprising said core material encapsulated with said wall material in said liquid and;

c. Recovering said colored encapsulated toner particles from said liquid.

* * * * *